(12) United States Patent
Yoshimura et al.

(10) Patent No.: US 8,119,839 B2
(45) Date of Patent: Feb. 21, 2012

(54) CARBOXYLIC ACID AND ANTIDEPRESSANT COMPOSITION CONTAINING THE SAME AS ACTIVE INGREDIENT

(75) Inventors: Hiroyuki Yoshimura, Toon (JP); Kiyoshi Okihara, Tomata-gun (JP); Satoshi Kawatake, Tomata-gun (JP); Hiroko Tani, Tomata-gun (JP); Tomoki Tatefuji, Tomata-gun (JP); Ken Hashimoto, Tomata-gun (JP); Hiromasa Tanaka, Tomata-gun (JP); Akinori Inoue, Tomata-gun (JP); Miyako Yanagihara, Tomata-gun (JP)

(73) Assignee: Yamada Apiculture Center, Inc., Okayama (JP)

( * ) Notice: Subject to any disclaimer, the term of this patent is extended or adjusted under 35 U.S.C. 154(b) by 0 days.

(21) Appl. No.: 12/669,584

(22) PCT Filed: Jul. 19, 2008

(86) PCT No.: PCT/JP2008/063073
§ 371 (c)(1),
(2), (4) Date: Mar. 17, 2010

(87) PCT Pub. No.: WO2009/014105
PCT Pub. Date: Jan. 29, 2009

(65) Prior Publication Data
US 2010/0184860 A1    Jul. 22, 2010

(30) Foreign Application Priority Data
Jul. 20, 2007 (JP) .................. 2007-189606

(51) Int. Cl.
C07C 57/02    (2006.01)
C07C 69/52    (2006.01)
A01N 37/00    (2006.01)
A01N 37/06    (2006.01)

(52) U.S. Cl. ......... 562/598; 560/205; 514/558; 514/549
(58) Field of Classification Search .................. None
See application file for complete search history.

(56) References Cited

U.S. PATENT DOCUMENTS
2005/0065212 A1    3/2005    Pineau

FOREIGN PATENT DOCUMENTS

| JP | S55-94317 A | 7/1980 |
|---|---|---|
| JP | H07-69879 | 3/1995 |
| JP | H09-67252 A | 11/1997 |
| JP | H10-114652 | 5/1998 |
| JP | H11-507661 A | 7/1999 |
| JP | 2004131407 | * 4/2004 |
| JP | 2004-534070 A | 11/2004 |

OTHER PUBLICATIONS

Winston et al., Journal of Chemical Ecology, vol. 8, No. 10, 1982.*

(Continued)

Primary Examiner — Karl J Puttlitz
(74) Attorney, Agent, or Firm — Roylance, Abrams, Berdo & Goodman, L.L.P.

(57) ABSTRACT

The present invention provides a novel compound and antidepressant composition that can be effectively used for improving depressed mood and depressed state, particularly for depressed mood and depressed state in menopausal women. The compound of the present invention is represented by the following formula (1):

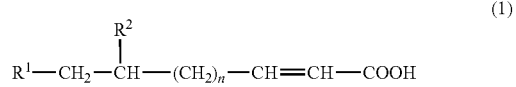

(1)

wherein $R^1$ and $R^2$ are identical or different and represent a hydrogen atom, a hydroxyl group or an acetyloxy group, and n is an integer of 2 to 7, or a pharmaceutically acceptable salt or ester thereof. This compound is used as an active ingredient in the antidepressant composition. Examples of the compound of the invention include (2E)-9,10-dihydroxy-2-decenoic acid, (2Z)-9,10-dihydroxy-2-decenoic acid, (2E)-9-hydroxy-2-decenoic acid, and (2E)-7-acetyloxy-2-heptenoic acid.

8 Claims, 6 Drawing Sheets

OTHER PUBLICATIONS

Database Caplus Chemical Abstracts Service, Columbus, Ohio, US; Database Accession No. 1979:22266 Abstract of Yokoi et al.: Nippon Kagaku Kaishi (1978), (10), 1415-20.*
Brown et al., Nature (1961) vol. 190, p. 88.*
Dhareshwar et al., Prodrugs of Alcohols and Phenols in "Prodrugs, Challenges and Rewards, Part 1", Springer, pp. 31-99.*
Okada et al., Jpn. J. Pharmacology, 73:93-96, 1997.
Yoshimura, Brain Science 22: 49-54, 2000.
Bekku et al., Psychopharmacology, 183:300-307, 2005.
Bekku et al., Japanese Journal of Psychopharmacology, 22: 299, 2002.
Porsort et al., Nature 266: 730-732 (1977).

* cited by examiner

Fig. 7

Isolation procedure of (2E)-9,10-dihydroxy-2-decenoic acid

RJ (200.4 g)
| MeOH 1.5L   400rpm   12hr
| filtration
| evaporated in vacuo
MeOH extract (108.9 g)
| ODS C.C. φ80 × 205 mm, 10%, 50%MeOH, each 2.5L (1.5 L × 2)
Fr. 50%-2 (9.2 g)
| Silica gel C.C. φ26 × 150 mm, 5% MeOH in CHCl$_3$ 500mL (50 mL × 10),
| MeOH 500mL
Frs. 7-10 (1.5 g)
| Silica gel C.C. φ26 × 150 mm, 5% MeOH in CHCl$_3$, each 600 mL (60
| mL × 10)
Fr. 5 (45.3 mg)
| prep. HPLC (Cosmosil C18-AR-II 10 × 250 mm, 13% Acetnitrile in 0.1% TFA,
| 5 mL/min, 220 nm)
DDA (13.3 mg)

Fig. 8

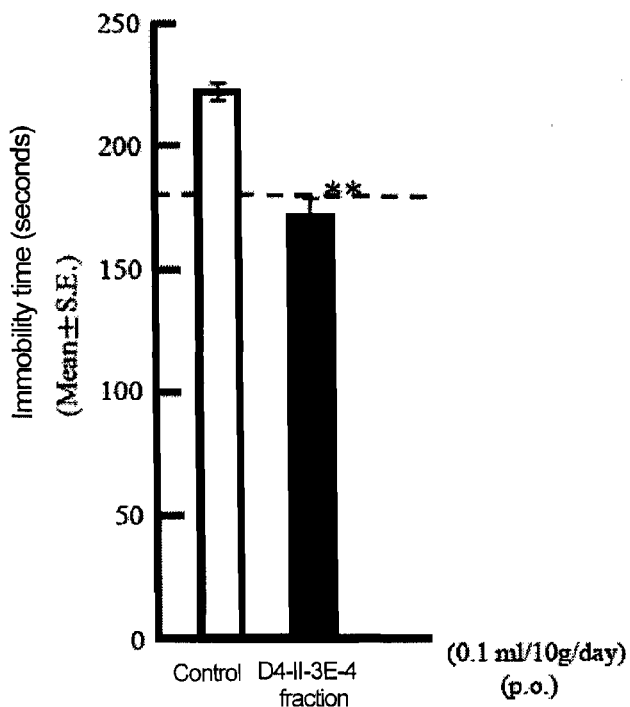

** $p < 0.01$; Significantly different from the vehicle-treated group.

\* : p<0.05
\*\* : p<0.01

CARBOXYLIC ACID AND ANTIDEPRESSANT COMPOSITION CONTAINING THE SAME AS ACTIVE INGREDIENT

TECHNICAL FIELD

The present invention relates to a novel carboxylic acid, and applications utilizing the pharmacological effects thereof. Specifically, the present invention relates to a novel carboxylic acid and a pharmaceutical composition comprising the carboxylic acid as an active ingredient, and particularly to an antidepressant agent effective for preventing or improving a depressed mood or depressed state. The present invention further relates to a method of effectively preventing or improving a depressed mood or depressed state.

BACKGROUND ART

In recent years, the number of people claiming mental aberrations has noticeably increased, reflecting a stressful society. In particular, the number of people suffering from a depressed mood or depressed state continues to increase as a result of workplace environmental changes as represented by technostress, increases in social stress, physical and mental overwork, disturbed rhythm of living, and the like. As a result of constant anxiety, tension, fretfulness, conflict, and the like, the symptoms of a depressed mood and depressed state are accompanied by affective disorder, in which people inappropriately express delight, anger, sorrow and pleasure; when left untreated, the disorder will develop into depression. It has been reported that about 10 to 15% of patients with depression commit suicide or attempt to do so, making depression an object of public concern.

Hitherto, drugs such as tricyclic antidepressants and monoamine oxidase inhibitors have been used in the treatment of depression. However, these drugs are likely to cause harmful side effects involving the autonomic nervous system and circulatory system; therefore, the long-term administration thereof, the administration in elderly people and the preventive administration thereof have remained difficult. Further, as mentioned above, improvements in depressed mood or depressed state at an early stage is important to prevent depression. However, because people may temporarily experience a depressed mood or depressed state due to environmental changes or when confronting various situations, the depressed mood or depressed state is generally not recognized as a disease. Therefore, preventive treatment therefor is unlikely to be offered until abnormal behavior is recognized. For this reason, an antidepressant that causes fewer side effects, and that enables long-term administration, administration in elderly people and preventive administration, is in demand.

It is known that 10-hydroxydecenoic acid, a compound similar to the carboxylic acid provided by the present invention, exhibits a variety of physiological activities. For example, Patent Document 1 discloses that 10-hydroxydecenoic acid exhibits aldose reductase inhibitory activities, which inhibit, in glucose metabolism, the conversion of glucose to sorbitol, and can thereby prevent or treat diabetes. Further, Patent Document 2 discloses that 10-hydroxydecenoic acid has Jin-Ye effects, i.e., effects of promoting secretion of water from the inside to the outside the body, thus exerting a variety of effects such as beautiful skin effect, hair-growth effect, digestive-juice secretion stimulatory effect, laxative effect, diuretic effect, and the like. However, the antidepressant effects in 10-hydroxydecenoic acid are unknown. Further, the experiments performed by the present inventors confirmed that 10-hydroxydecenoic acid exhibits no antidepressant effects (see Test Example 1 described hereunder).

Patent Document 1: Japanese Unexamined Patent Publication No. H7-69879
Patent Document 2: Japanese Unexamined Patent Publication No. H10-114652

DISCLOSURE OF THE INVENTION

Problems to be Solved by the Invention

It is an object of the present invention to provide a novel compound, in particular, a compound having an antidepressant effect, which can be effectively utilized as an active ingredient in a pharmaceutical composition such as an antidepressant. It is also an object of the present invention to provide an antidepressant composition that comprises the above-mentioned compound as an active ingredient, and that can be effectively utilized for improving a depressed mood or depressed state, particularly a depressed mood or depressed state in menopausal women. It is further an object of the present invention to provide an antidepressant composition that causes fewer side effects and that enables long-term administration.

Means for Solving the Problems

The present inventors conducted extensive research to achieve the above objects, and found that a novel carboxylic acid, particularly novel carboxylic acids such as (2E)-9,10-dihydroxy-2-decenoic acid, (2Z)-9,10-dihydroxy-2-decenoic acid, (2E)-9-hydroxy-2-decenoic acid and (2E)-7-acetoxy 2-heptenoic acid, exhibit excellent antidepressant effects and are effective for alleviating depressed mood or depressed state, particularly in menopausal women. The novel carboxylic acid is represented by the following formula (1):

[Chem. 1]

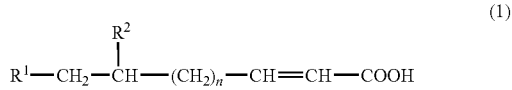

wherein $R^1$ and $R^2$ are identical or different, and represent a hydrogen atom, a hydroxyl group or an acetyloxy group, and n is an integer of 2 to 7. The present invention has been accomplished based on such findings, and encompasses the following aspects.

(I) Novel Carboxylic Acid, or Pharmaceutically Acceptable Salt or Ester Thereof (I-1) A carboxylic acid represented by the following Formula (1):

[Chem. 2]

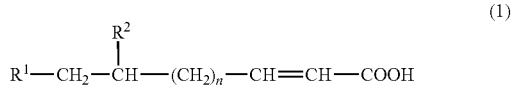

wherein $R^1$ and $R^2$ are identical or different, and represent a hydrogen atom, a hydroxyl group or an acetyloxy group, and n is an integer of 2 to 7, or a pharmaceutically acceptable salt or ester thereof.

(I-2) The carboxylic acid, or the pharmaceutically acceptable salt or ester thereof according to (I-1), wherein the carboxylic acid is a compound selected from the group consisting of (2E)-9,10-dihydroxy-2-decenoic acid, (2Z)-9,10-dihydroxy-2-decenoic acid, (2E)-9-hydroxy-2-decenoic acid and (2E)-7-acetoxy-2-heptenoic acid.

(I-3) The carboxylic acid, or the pharmaceutically acceptable salt or ester thereof according to (I-2), wherein the (2E)-9,10-dihydroxy-2-decenoic acid is (2E,9R)-9,10-dihydroxy-2-decenoic acid, (2E,9S)-9,10-dihydroxy-2-decenoic acid or a mixture thereof.

(I-4) The carboxylic acid, or the pharmaceutically acceptable salt or ester thereof according to (I-2), wherein the (2Z)-9,10-dihydroxy-2-decenoic acid is (2Z,9R)-9,10-dihydroxy-2-decenoic acid, (2Z,9S)-9,10-dihydroxy-2-decenoic acid or a mixture thereof.

(I-5) The carboxylic acid, or the pharmaceutically acceptable salt or ester thereof according to (I-2), wherein the (2E)-9-hydroxy-2-decenoic acid is (2E,9R)-9-hydroxy-2-decenoic acid, (2E,9S)-9-hydroxy-2-decenoic acid, or a mixture thereof.

(II) A Composition Containing the Above-Mentioned Novel Carboxylic Acid Etc. as an Active Ingredient (II-1) A pharmaceutical composition comprising, as an active ingredient, the carboxylic acid, or the pharmaceutically acceptable salt or ester thereof in accordance with any of (I-1) to (I-5).

(II-2) The pharmaceutical composition according to (II-1), which is an antidepressant.

(II-3) The pharmaceutical composition according to (II-1) or (II-2), which is administered to a menopausal woman in order to prevent or improve menopausal depressed mood or depressed state in women.

(II-4) An antidepressant composition comprising, as an active ingredient, the carboxylic acid, or the pharmaceutically acceptable salt or ester thereof in accordance with any of (I-1) to (I-5).

(II-5) The antidepressant composition according to (II-4), which is administered to a menopausal woman in order to prevent or improve menopausal depressed mood or depressed state in women.

(III) Application of the Above-Mentioned Novel Carboxylic Acid Etc.

(III-1) The carboxylic acid, or the pharmaceutically acceptable salt or ester thereof according to (I-1) to (I-5), which is used for preventing or improving depressed mood or depressed state.

(III-2) The carboxylic acid, or the pharmaceutically acceptable salt or ester thereof according to any of (I-1) to (I-5), which is administered to a menopausal woman in order to prevent or improve menopausal depressed mood or depressed state in women.

(III-3) Use of the carboxylic acid, or the pharmaceutically acceptable salt or ester thereof in accordance with any of (I-1) to (I-5), for preparation of a pharmaceutical composition.

(III-4) The use according to (III-3), wherein the pharmaceutical composition is an antidepressant.

(III-5) The use according to (III-4), wherein the antidepressant prevents or improves menopausal depressed mood or depressed state in women.

(III-6) Use of the carboxylic acid, or the pharmaceutically acceptable salt or ester thereof in accordance with any of (I-1) to (I-5), for preparation of an antidepressant composition.

(III-7) The use according to (III-6), wherein the antidepressant composition prevents or improves menopausal depressed mood or depressed state in women.

(IV) Antidepressant Method (IV-1) A method for preventing or improving depressed mood or depressed state, comprising administering the carboxylic acid, or the pharmaceutically acceptable salt or ester thereof in accordance with claims 1 to 5 to a person in a depressed mood or depressed state.

(IV-2) A method for preventing or improving menopausal depressed mood or depressed state, comprising administering the carboxylic acid, or the pharmaceutically acceptable salt or ester thereof in accordance with claims 1 to 5 to a menopausal woman.

Effect of the Invention

The present invention can provide a novel compound that has an antidepressant effect and that is useful as an active ingredient in pharmaceutical compositions, particularly antidepressants. The present invention can further provide an antidepressant composition comprising the above compound as an active ingredient. The antidepressant composition can be effectively used for improving menopausal depressed mood or depressed state in women.

In particular, (2E)-9,10-dihydroxy-2-decenoic acid, an active ingredient contained in the composition of the present invention having an antidepressant effect, exhibits an excellent antidepressant effect and is highly safe, causing fewer side effects while enabling long-term use. For this reason, the composition of the present invention is also effectively used for prophylactic purposes in addition to improving depressed mood or depressed state.

BEST MODE FOR CARRYING OUT THE INVENTION (I) Novel Carboxylic Acid, or a Pharmaceutically Acceptable Salt or Ester Thereof The novel compounds of the present invention are carboxylic acids represented by the following formula (1):

[Chem. 3]

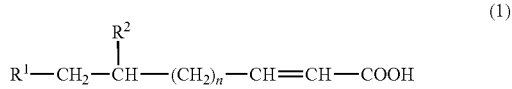

(1)

wherein $R^1$ and $R^2$ are identical or different and represent a hydrogen atom, a hydroxyl group or an acetyloxy group, and n is an integer of 2 to 7.

As described above, $R^1$ and $R^2$ may be identical and represent hydrogen atoms, hydroxyl groups or acetyloxy groups; or may each represent a different group (a hydrogen atom, a hydroxyl group or an acetyloxy group). $R^1$ is preferably a hydrogen atom, a hydroxyl group or an acetyloxy group, and more preferably a hydrogen atom or a hydroxyl group. $R^2$ is preferably a hydrogen atom or a hydroxyl group, and more preferably a hydroxyl group. In a combination of $R^1$ and $R^2$, when $R^1$ is a hydrogen atom or a hydroxyl group, $R^2$ is preferably a hydroxyl group; when $R^1$ is an acetyloxy group, $R^2$ is preferably a hydrogen atom.

As described above, n may be any integer from 2 to 7, but is preferably selected from 2 to 5.

Compound (1) of the present invention may be in the cis- or trans-configuration, and compound (1) of the present invention encompasses both the cis and trans isomers thereof. In compound (1) of the present invention, a compound wherein R¹ is a hydrogen atom or a hydroxyl group and R² is a hydroxyl group encompasses enantiomers (R- and S-forms) wherein the carbon at the 2-position from R¹ residue is a chiral center. Specifically, in compound (1) of the present invention, a compound wherein R¹ is a hydrogen atom or a hydroxyl group and R² is a hydroxyl group may be either of the R- or S-enantiomer, wherein the carbon at the 2-position from R¹ residue is a chiral center; or may be a mixture, e.g., a racemic compound, containing the R- and S-enantiomers in a desired proportion.

Compound (1) encompasses, but is not limited to, the following compounds ((1a) to (1f)) specifically shown below:

[Chem. 4]

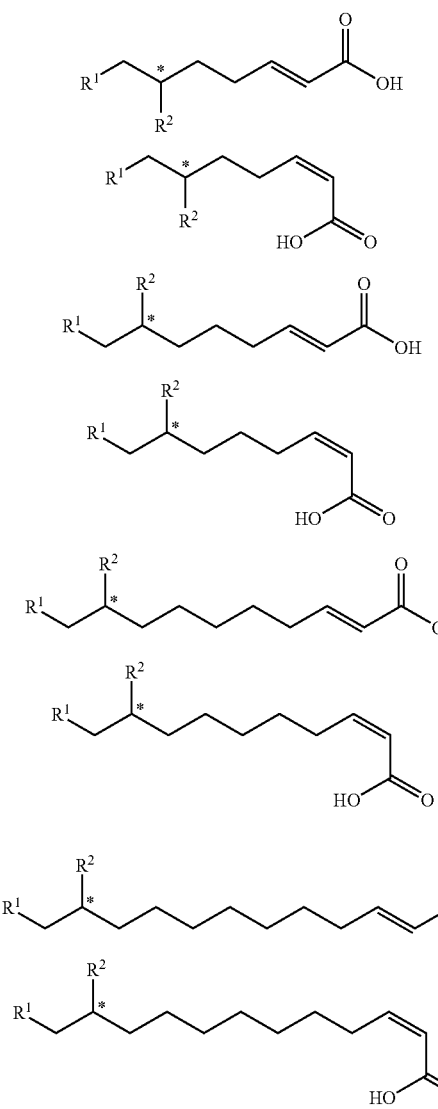

wherein R¹ and R² are identical or different, and represent a hydrogen atom, a hydroxyl group or an acetyloxy group. In the formulae, the carbons marked with an asterisk are a chiral center (asymmetric carbon). The compounds represented by the above formulae encompass both the R- and S-forms. Of these, (2E)-9,10-dihydroxy-2-decenoic acid represented by the following formula is preferred, the compound of which is of the above formula (1e) or (1f), wherein R¹ and R² are hydroxyl groups.

[Chem. 5]

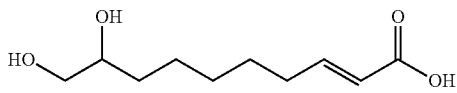

The (2E)-9,10-dihydroxy-2-decenoic acid may be mirror-image isomers (enantiomers), which are R-enantiomer ((2E,9R)-9,10-dihydroxy-2-decenoic acid) represented by the following formula (ii), and S-enantiomer ((2E,9S)-9,10-dihydroxy-2-decenoic acid) represented by the following formula (i).

[Chem. 6]

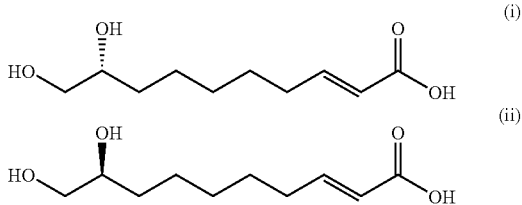

The (2E)-9,10-dihydroxy-2-decenoic acid of the present invention may be either of the enantiomers, i.e., R-enantiomer ((2E,9R)-9,10-dihydroxy-2-decenoic acid)) or S-enantiomer ((2E,9S)-9,10-dihydroxy-2-decenoic acid)); or may be a mixture, e.g., a racemic mixture, of the above-mentioned enantiomers in desired proportions.

Further, (2E)-9-hydroxy-2-decenoic acid represented by the following formula, whose compound is of the above formula (1e) or (1f) wherein R¹ is a hydrogen atom and R² is a hydroxyl group, is preferred.

[Chem. 7]

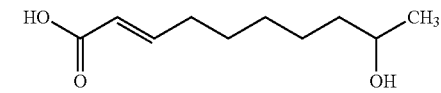

The (2E)-9-hydroxy-2-decenoic acid may be mirror-image isomers (enantiomers), which are R-enantiomer ((2E,9R)-9-hydroxy-2-decenoic acid) represented by the following formula (iii), and S-enantiomer ((2E,9S)-9-hydroxy-2-decenoic acid) represented by the following formula (iv).

[Chem. 8]

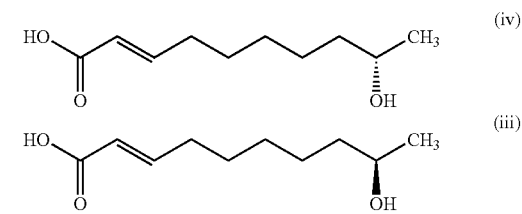

The (2E)-9-dihydroxy-2-decenoic acid of the present invention may be either of the enantiomers, i.e., R-enantiomer ((2E,9R)-9,10-dihydroxy-2-decenoic acid)) or S-enantiomer ((2E,9S)-9,10-dihydroxy-2-decenoic acid)); or may be a mixture, e.g., a racemic mixture, of the above-mentioned enantiomers in desired proportions.

Further, (2E)-7-acetoxy-2-heptenoic acid represented by the following formula, whose compound is of the above formula (1a) or (1b) wherein $R^1$ is an acetyloxy group and $R^2$ is a hydrogen atom, is preferred.

[Chem. 9]

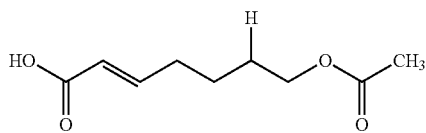

Compound (1) of the present invention may be in free carboxylic acid, or a pharmaceutically acceptable salt or an ester.

Examples of pharmaceutically acceptable salts usable herein include salts with inorganic or organic bases; and salts with basic amino acids. Examples of inorganic bases include alkali metal salts such as sodium, potassium and the like; alkaline earth metal salts such as calcium, magnesium and the like; and ammonium salts and aluminum salts. Examples of organic bases include primary amines such as ethanolamine and the like; secondary amines such as diethylamine, diethanolamine, dicyclohexylamine, N,N'-dibenzylethylenediamine and the like; and tertiary amines such as trimethylamine, triethylamine, triethanolamine, pyridine, picoline and the like. Examples of basic amino acids include lysine, arginine, ornithine, and the like. Examples of esters include $C_1$ to $C_6$ lower alkyl esters of the carboxylic acids (for example, methyl esters, ethyl esters and n-propyl esters); $C_1$ to $C_6$ lower alkyl thioesters of the carboxylic acids (for example, methylthio esters, ethyl thioesters and n-propyl thioesters); and di- or oligoesters of the corresponding carboxylic acids.

Among the compounds represented by formula (1) of the present invention, compounds wherein both $R^1$ and $R^2$ represent hydroxyl groups may be prepared according to the method shown in the following reaction scheme 1 by, for example, using commercially available 4-(2-hydroxyethyl)-2,2-dimethyl-1,3-dioxolane (2) as a starting material.

Reaction Scheme 1

[Chem. 10]

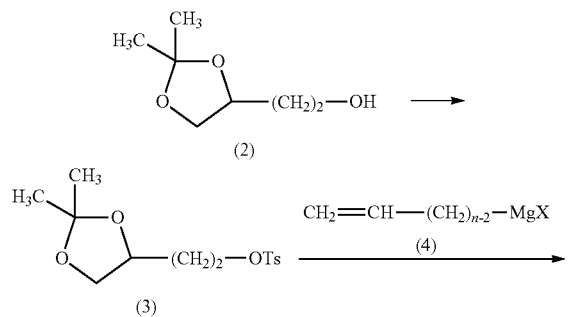

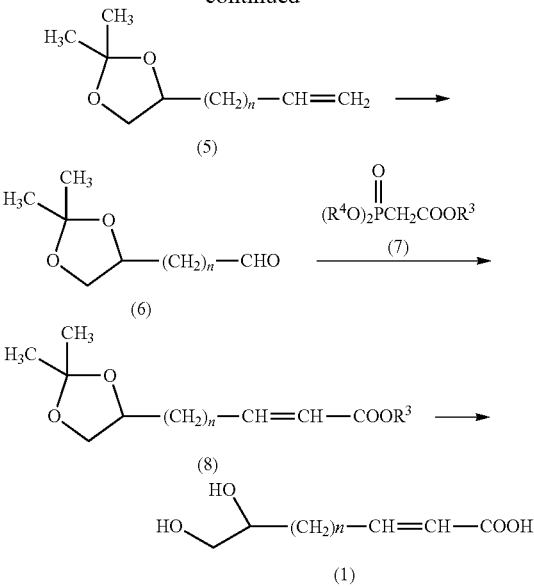

wherein Ts is a tosyl group, X is a halogen atom, $R^3$ and $R^4$ are identical or different and represent a C1-6 alkyl group, and n is the same as defined above.

Compound (3) may be prepared by reacting compound (2) with a p-tosyl halide. Examples of p-tosyl halides include p-tosyl chloride, p-tosyl bromide and the like. It is usually preferable that p-tosyl halide is used in an amount of about 0.5 to about 2 mol per 1 mol of compound (2). This reaction is generally performed in a suitable inert solvent. As the inert solvent, known solvents that do not have an adverse effect on the reaction may be widely utilized. Examples thereof include pyridine, tetrahydrofuran and the like. The reaction suitably proceeds at a temperature of from about −10° C. to about 10° C., and is generally completed in about 5 to about 10 hours.

Compound (5) may be prepared by reacting compound (3) with easily available known compound (4). The X in the formula of compound (4) may be, for example, chlorine, bromine, or the like. It is generally preferable that compound (4) is used in an amount of about 0.5 to about 2 mol, per 1 mol of compound (3). The reaction is generally performed in a suitable inert solvent in the presence of a catalyst. As the inert solvent, known solvents that do not have an adverse effect on the reaction may be widely utilized. Examples thereof include tetrahydrofuran, ether and the like. Examples of catalysts include copper iodide and the like. The reaction suitably proceeds at a temperature of from room temperature to about 50° C., and is generally completed in about 2 to about 5 hours.

Compound (6) may be prepared by reacting compound (5) with ozone, and subsequently reacting the obtained compound with methyl sulfide. The reaction between compound (5) and ozone is generally performed in a suitable inert solvent. As the inert solvent, known solvents that do not have an adverse effect on the reaction may be widely utilized. Examples thereof include methylene chloride, methanol and the like. The reaction suitably proceeds at a temperature of from about −80° C. to about −70° C., and is generally completed in about 10 minutes to about 1 hour. The subsequent reaction with methyl sulfide is performed in the same solvent as that used in the reaction between compound (5) and ozone. The reaction suitably proceeds at a temperature of from about −80° C. to about room temperature, and is generally completed in about 2 to about 8 hours.

Compound (8) may be prepared by reacting compound (6) with easily available known compound (7). It is generally preferable that compound (7) is used in an amount of about 0.5 to about 2 mol, per 1 mol of compound (6). This reaction is generally performed in a suitable inert solvent in the presence of a catalyst. As the inert solvent, known solvents that do not have an adverse effect on the reaction may be widely utilized. Examples thereof include tetrahydrofuran, dimethyl sulfoxide, and the like. Examples of catalysts include sodium hydride and the like. The reaction suitably proceeds at a temperature of from about −10° C. to about 10° C., and is generally completed in about 2 to about 5 hours.

Compound (1) (a compound of formula (1) wherein $R^1$ and $R^2$ are both hydroxyl groups) may be prepared by reacting compound (8) with trifluoroacetic acid, and then allowing a base to act on the obtained compound. The reaction between compound (8) and trifluoroacetic acid is generally performed in a suitable inert solvent. As the inert solvent, known solvents that do not have an adverse effect on the reaction may be widely utilized. Examples thereof include methylene chloride, dichloromethane, methanol and the like. The reaction suitably proceeds at a temperature of from about −10° C. to about 10° C., and is generally completed in about 3 to about 10 hours. Examples of usable bases include known alkalis such as potassium hydroxide, sodium hydroxide and the like. A treatment with a base is performed in, for example, an alcohol such as methanol, ethanol and the like. A treatment with a base is usually performed for about 1 to about 5 hours at about room temperature.

Among compounds represented by formula (1) of the present invention, a compound wherein either $R^1$ or $R^2$ is a hydrogen atom or an acetyloxy group may be prepared by converting the hydroxyl group of the above-mentioned compound (1) into a hydrogen atom or an acetyloxy group. Specifically, the compound may be prepared in accordance with the method shown in the Preparation Examples 3 to 6 described hereunder.

The salts and ester bodies of the present invention may be prepared in accordance with a standard method from the carboxylic acids obtained in the methods described above. For example, an ester body can be prepared by reacting the above-mentioned carboxylic acid with an alcohol or thiol.

The compound of formula (1) of the present invention may be isolated and purified from natural products containing the compounds. Specifically, (2E)-9,10-dihydroxy-2-decenoic acid represented by formula (i) or (ii) may be isolated and purified from royal jelly, as shown in Preparation Examples 1 and 2 below. However, so long as the compound can be isolated, the methods are not limited thereto.

(II) Pharmaceutical Composition and Antidepressant Composition

The pharmaceutical composition and antidepressant composition of the present invention contain, as an active ingredient, the compound of formula (1) above, or a pharmaceutically acceptable salt or ester thereof. The pharmaceutical composition and antidepressant composition may contain compound (1) in the form of solvate, for example, a hydrate.

Compound (1) is preferably (2E)-9,10-dihydroxy-2-decenoic acid, (2Z)-9,10-dihydroxy-2-decenoic acid, (2E)-9-hydroxy-2-decenoic acid or (2E)-7-acetoxy-2-heptenoic acid. The composition of the present invention may consist of 100% of the above compound, or a pharmaceutically acceptable salt or ester thereof (hereunder collectively referred to as "DDA"). Alternatively, the composition of the present invention may comprise DDA in an amount effective for exerting an antidepressant effect. Although not limited thereto, the DDA content in the composition of the present invention is usually 0.001 to 99 wt. %, and preferably 0.01 to 80 wt. %.

The antidepressant composition of the present invention is effective as a pharmaceutical composition for particularly improving a depressed state or treating depression. The depressed state used herein refers to states of symptoms such as "depressed mood (depressed feeling or unpleasant feeling that is not dispelled no matter what is done; empty feeling and sadness)" and "loss of interest and joy (a state of feeling paralyzed, unable to find joy in what used to be enjoyable)". A person will be diagnosed as suffering from depression when experiencing one of the above major symptoms as well as the following symptoms over a long period of time: "feelings of worthlessness, i.e., finding no value in oneself", "suicidal ideation and suicidal feelings", "decrease in energy and fatigability", "decline in concentration, thinking power and decision-making ability", and "physical symptoms such as loss of appetite and insomnia". A diagnosis of depression may also be made according to, for example, DSM-IV-TR (Diagnostic and Statistical Manual of Mental Disorders), published by the American Psychiatric Association.

In such a depressed state or depression, the antidepressant composition of the present invention is effective for preventing, improving or treating menopausal depressed state or depression in women. During menopause, ovarian function is reduced, producing lower levels of female hormones (estrogen). Such a rapid decrease in female hormone production is prone to lead to both physical and emotional instability. This is considered to be the cause of the depressed state and susceptibility to depression. In view of the above, the antidepressant composition of the present invention can be advantageously applied to menopausal women experiencing a depressed state or suffering from depression.

The antidepressant composition of the present invention is usually prepared using a pharmaceutically acceptable carrier or an additive, in addition to DDA in an amount effective for preventing and improving a depressed state, or treating depression. The amount of DDA contained in the composition is suitably determined depending on the type and severity of the target depressed state, and the administration form; however, for a systemically administered preparation, the amount may usually be 0.001 to 50 wt. %, preferably 0.01 to 10 wt. %, relative to the total weight of the antidepressant composition (100 wt. %).

Examples of administration methods of the antidepressant composition of the present invention include parenteral administrations such as oral administration, intravenous administration, intramuscular administration, subcutaneous administration, transmucosal administration, percutaneous administration, intrarectal administration and the like. Of these, oral administration and intravenous administration are preferable, and oral administration is more preferable. The antidepressant composition of the present invention may be prepared in various forms of preparations (dosage forms), depending on the above-mentioned administration method. Each preparation form (dosage form) will be described below; however, the dosage forms usable in the present invention are not limited thereto, and various dosage forms that are generally utilized in the field of pharmaceutical preparations may be used.

The dosage forms for oral administration may be, for example, powders, granules, capsules, pills, tablets, elixirs, suspensions, emulsions, and syrups, and may be suitably selected therefrom. Further, such preparations may be modified so as to be sustained-release, stabilized, easily disintegrated, slowly disintegrated, enteric-coated, easily absorbed, and the like.

The dosage forms for intravenous administration, intramuscular administration and subcutaneous administration may be injections, drip feeds (including dry products of extemporaneous preparations) or the like, and may be suitably selected therefrom.

The dosage forms for transmucosal administration, percutaneous administration and intrarectal administration may be peptizers, sublingual formulations, buccal formulations, troche agents, ointments, patch agents, liquid agents and the like, and may be suitably selected depending on where to apply. Such preparations may be modified so as to be sustained-release, stabilized, easily disintegrated, slowly disintegrated, easily absorbed, and the like.

The antidepressant composition of the present invention may comprise a pharmaceutically acceptable carrier and an additive, depending on the dosage form (dosage forms of oral administration or various types of parenteral administrations). Examples of pharmaceutically acceptable carriers and additives include solvents, excipients, coating agents, bases, binders, lubricants, disintegrants, solubilizing agents, suspending agents, thickeners, emulsifiers, stabilizers, buffers, tonicity agents, soothing agents, preservatives, corrigents, fragrances, and coloring agents. Hereunder, examples of pharmaceutically acceptable carriers and additives are specifically exemplified, but the present invention is not limited thereto.

Examples of solvents include purified water, sterile purified water, water for injection, physiological saline solution, peanut oil, ethanol, glycerin and the like. Examples of excipients include starches (for example, potato starch, wheat starch and corn starch), lactose, glucose, sucrose, crystalline cellulose, calcium sulfate, calcium carbonate, sodium hydrogencarbonate, sodium chloride, talc, titanium oxide, trehalose, xylitol, and the like.

Examples of binders include starches and derivatives thereof, cellulose and derivatives thereof (for example, methyl cellulose, ethyl cellulose, hydroxypropyl cellulose, carboxymethyl cellulose), gelatin, sodium alginate, tragacanth, gum arabic, and like natural polymer compounds, polyvinylpyrrolidone, polyvinyl alcohol, and like synthetic polymer compounds, dextrin, hydroxypropyl starch, and the like.

Examples of lubricants include light anhydrous silicic acid, stearic acid and salts thereof (for example, magnesium stearate), talc, waxes, wheat starch, macrogol, hydrogenated vegetable oil, sucrose esters of fatty acids, polyethylene glycol, silicone oil, and the like.

Examples of disintegrants include starches and derivatives thereof, agar, gelatin powder, sodium hydrogencarbonate, calcium carbonate, cellulose and derivatives thereof, hydroxypropyl starch, carboxymethyl cellulose and salts thereof, crosslinked carboxymethyl cellulose, low-substitutional hydroxypropyl cellulose, and the like.

Examples of solubilizing agents include cyclodextrin, ethanol, propylene glycol, polyethylene glycol and the like. Examples of suspending agents include sodium carboxymethylcellulose, polyvinylpyrrolidone, gum arabic, tragacanth, sodium alginate, aluminum monostearate, citric acid, various surfactants, and the like.

Examples of thickeners include sodium carboxymethylcellulose, polyvinylpyrrolidone, methyl cellulose, hydroxypropyl methylcellulose, polyvinyl alcohol, tragacanth, gum arabic, sodium alginate, and the like.

Examples of emulsifiers include gum arabic, cholesterol, tragacanth, methyl cellulose, lecithin, various surfactants (for example, polyoxyl 40 stearate, sorbitan sesquioleate, polysorbate 80, sodium lauryl sulfate), and the like.

Examples of stabilizers include tocopherol, chelating agents (for example, EDTA, thioglycolic acid), inert gases (for example, nitrogen, carbon dioxide), reducing agents (for example, sodium hydrogen sulfite, sodium thiosulfate, ascorbic acid, rongalite), and the like.

Examples of buffers include sodium dihydrogenphosphate, sodium acetate, sodium citrate, boric acid, and the like.

Examples of tonicity agents include sodium chloride, glucose and the like. Examples of soothing agents include local anesthetics (procaine hydrochloride, lidocaine), benzyl alcohol, glucose, sorbitol, amino acid, and the like.

Examples of corrigents include sucrose, saccharin, *Glycyrrhiza* extract, sorbitol, xylitol, glycerin and the like. Examples of fragrances include orange peel tincture, rose oil and the like. Examples of coloring agents include water-soluble food colorants, lake colorants, and the like.

Examples of preservatives include benzoic acids and salts thereof, p-hydroxybenzoate esters, Chlorobutanol, invert soap, benzyl alcohol, phenol, thimerosal, dehydroacetic acid, boric acid, and the like.

Examples of coating agents include sucrose, hydroxypropyl cellulose (HPC), shellac, gelatin, glycerin, sorbitol, hydroxypropyl methylcellulose (HPMC), ethyl cellulose, polyvinylpyrrolidone (PVP), hydroxypropylmethylcellulose phthalate (HPMCP), cellulose acetate phthalate (CAP), methyl methacrylate/methacrylate copolymers, the aforementioned polymers, and the like.

Examples of bases include Vaseline, liquid paraffin, carnauba wax, beef tallow, hardened oil, paraffin, beeswax, vegetable oil, macrogol, macrogol fatty acid ester, stearic acid, sodium carboxymethylcellulose, bentonite, cacao butter, witepsol, gelatin, stearyl alcohol, hydrous lanolin, cetanol, light liquid paraffin, hydrophilic petrolatum, simple ointment, white ointment, hydrophilic ointment, macrogol ointment, hard fat, oil-in-water emulsified base, water-in-oil emulsified base, and the like.

The techniques used in a known drug delivery system (DDS) may be applied to each of the above-mentioned dosage forms. The DDS preparation used herein refers to a preparation prepared in optimal dosage form, such as a controlled-released preparation, a topically applied preparation (troches, buccal tablets, sublingual tablets, etc.), a drug-release control preparation, an enteric-coated preparation, a gastric-soluble preparation, and the like, in consideration of administration routes, bioavailability, side effects, and the like.

The amount of the antidepressant composition of the present invention for oral administration is preferably in the range of from 0.01 to 100 mg/kg, and more preferably from 0.02 to 10 mg/kg, in terms of the amount of carboxylate-free compound (1). The amount for intravenous administration is, for example, an amount such that the effective blood concentration of a carboxylate-free compound (1) is in the range of from 0.01 to 1,000 µg/mL, and more preferably in the range of from 0.02 to 100 µg/mL. The above administration amounts may vary depending on the age, gender, physique, etc. of the person.

EXAMPLES

Hereunder, the present invention is described in more detail with reference to Preparation Examples, Test Examples and Examples, but is not limited thereto.

Preparation Example 1

Preparation of (2E)-9,10-dihydroxy-2-decenoic acid

In accordance with the method shown in (1) to (6) below, (2E)-9,10-dihydroxy-2-decenoic acid was isolated and purified from royal jelly (see FIGS. 1 to 6).

The apparatus used in the isolation and purification was shown below.

High-speed refrigerated centrifuge: CR-21, product of Hitachi, Ltd. Rotor: R10A

Ultrafiltration membrane: Prep/Scale-TFF Cartridge PLGC10k 1 ft$^2$, product of Millipore Corporation Pump: Roller pump customized for a filtration membrane, product of Millipore Corporation Freeze dryer: FDU-540, product of Tokyo Rikakikai Co, Ltd.

(1) Preparation of A3 Fraction Using Ultrafiltration Membrane

Ion exchange water (1.5 L) was added to a dried royal jelly powder (about 150 g), and stirred at room temperature for 2 hours. The resulting product was subjected to centrifugal separation (10,000 rpm, 18,780×g, 10 minutes) using a high-speed refrigerated centrifuge to be fractionated into water-soluble and insoluble fractions. Ion exchange water (0.5 L) was added to the obtained insoluble fraction, and the same procedure was repeated twice (with a proviso that each stirring time was 30 minutes).

The insoluble fraction finally retained was referred to as B1 fraction; and the water-soluble fractions retained as a result of the procedure repeated three times were collectively referred to as A1 fraction. A1 fraction was fractionated through a 10-kDa ultrafiltration membrane into A3 fraction having a molecular weight of 10,000 or less.

The procedure was repeated 5 times as above, and 454 g of A3 fraction (a freeze-dried product) was obtained from 774 g of royal jelly dry powder.

(2) Fractionation Procedure from A3 Fraction Using Gel Filtration (FIG. 2)

Ion exchange water (100 ml) was added to the A3 fraction (a freeze-dried product: 30 to 35 g) prepared in (1), and stirred at room temperature for 30 minutes. Thereafter, the resulting product was subjected to centrifugal separation (10,000 rpm, 4° C., 10 minutes) to be fractionated into the supernatant and the precipitate (D5).

The supernatant was supplied to a gel filtration column (Tosoh Corporation: Toyopeal HW40F, 2 liter, column size: ø50×1,000 mm), and an eluent (ion exchange water) was applied thereto at a flow rate of 8 ml/min. While detecting with UV at a wavelength of 210 nm, the fractionation was performed for every 100 ml thereof. The fraction collected from 0.3 to 1.2 L was referred to as D1 fraction, that collected from 1.3 to 2.6 L was referred to as D2 fraction, that collected from 2.7 to 4.4 L was referred to as D3 fraction, and that collected from 4.5 to 5.0 L was referred to as D4 fraction.

This procedure was repeated 13 times, and 4.66 g of D4 fraction (a freeze-dried product) was obtained from 417.4 g of the A3 fraction (a freeze-dried product).

(3) Fractionation Procedure from D4 Fraction by Reversed-Phase Medium-Pressure Chromatography (ODS) (FIG. 3)

The D4 fraction prepared in (2) was dissolved in an equimolar mixed liquid of acetonitrile and a 0.1% aqueous trifluoroacetic acid solution (1:1), and fractionated under the following conditions using a preparative reversed-phase column (Hi-Flash Column ODS-8-50 W-L (36 g, 2.6×100 mm)) by preparative medium-pressure chromatography (Yamazen Corporation: YFLC-Wprep2XY-W 10V).

Chromatography Conditions

Flow rate: 20 ml/min, fractionations performed every 1 minute

Elution solvent: acetonitrile: 0.1% aqueous trifluoroacetic acid solution (98:2 (8 minutes)→0.01 minute→100:0 (10 minutes))

Detection: UV 254 nm

The fraction that was not adsorbed onto a column with the use of a mixed liquid of acetonitrile and a 0.1% aqueous trifluoroacetic acid solution (2:98) was referred to as D4-I fraction, and the fraction eluted through an acetonitrile (100%) was referred to as D4-II fraction. The same procedure was repeated 3 times, and D4-I fraction (a freeze-dried product) (0.81 g) and D4-II fraction (a freeze-dried product) (2.26 g) were obtained from the D4 fraction (a freeze-dried product) (2.76 g).

(4) Fractionation Procedure from D4-II Fraction by Reversed-Phase High-Performance Liquid Chromatography (ODS) (FIG. 4)

The D4-II fraction prepared in (3) was dissolved in a mixed liquid of acetonitrile and a 0.1% aqueous trifluoroacetic acid solution (2:5), which was purified by high-performance liquid chromatography (HPLC) under the following conditions.

HPLC Conditions

HPLC device: Waters Delta 600

Detector: Waters 2996 (Photodiode array detector)

Preparative column: Nacalai Tesque Cosmosil 5C18-AR-II (ø10×250 mm)+guard column (10×10 mm)

Flow rate: 5 ml/min

Detection: PDA Max plot

Elution condition: acetonitrile: 0.1% aqueous trifluoroacetic acid solution (0:100 (10 minutes)→50 minute→100:0 (20 minutes)).

Separation was performed by HPLC under the above-mentioned elution condition, and fractionation was carried out every 10 minutes; thereby, 8 fractions in total (D4-II-1 to D4-II-8) were obtained. The above preparative separation procedure was repeated, and D4-II-3 fraction (a freeze-dried product) (6.8 mg) was obtained from the D4-II fraction (a freeze-dried product) (49.3 mg).

(5) Fractionation Procedure from D4-II-3 Fraction by Reversed-Phase High-Performance Liquid Chromatography (ODS) (FIG. 5)

The D4-II-3 fraction prepared in (4) was dissolved in a mixed liquid of acetonitrile and a 0.1% aqueous trifluoroacetic acid solution (1:1), which was then purified by high-performance liquid chromatography (HPLC) under the following conditions:

HPLC Conditions

HPLC device: Waters Delta 600

Detector: Waters 2996 (Photodiode array detector)

Preparative column: Nacalai Tesque Cosmosil 5C18-AR-II (ø10×250 mm)+guard column (10×10 mm)

Flow rate: 5 ml/min

Detection: PDA Max plot

Elution condition: acetonitrile: 0.1% aqueous trifluoroacetic acid solution (13:87 (30 minutes)→10 minute→0:100 (10 minutes)).

Separation was performed by HPLC under the above-mentioned elution condition, and fractionation was performed using the chromatographic peak as an index; thereby, 8 fractions in total (D4-II-3A to D4-II-3H) were obtained. The above preparative separation procedure was repeated, and D4-II-3E fraction (a freeze-dried product) (0.9 mg) was obtained from the D4-II-3 fraction (a freeze-dried product) (15.6 mg).

(6) Separation from D4-II-3E Fraction by the Normal Phase Chromatography (FIG. 6)

The D4-II-3E fraction (a freeze-dried product) (16.6 mg) prepared in (5) was dissolved in 0.5 ml of an equimolar mixed solution of chloroform and methanol (1:1), and then purified by normal phase column chromatography under the following conditions.

Normal Phase Column Chromatography Conditions

Silica for separation: Silica gel BW-300 (5 g), product of Fuji Silysia Chemical Ltd.

Size: ø15×44 mm

Elution condition: chloroform:methanol (95:5 (35 ml)→9:1 (15 ml))

Under the above-mentioned elution condition, fractionations were performed for 2 ml each of an eluent by thin layer chromatography using an anisaldehyde sulfuric acid reagent for visualization. Thereby, 4 fractions in total (D4-II-3E-1 to D4-II-3E-4) were obtained. The above purifying procedure was repeated, and D4-II-3E-4 fraction (a freeze-dried product) (3.3 mg) was obtained.

(7) Identification of D4-II-3E-4 Fraction

The D4-II-3E-4 fraction obtained in (6) above was subjected to FAB-MS measurement (JEOL Ltd.: JMS-T100LC (matrix: polyethylene glycol)), $^1$H-NMR measurement (JEOL Ltd.: ECP-500) and $^{13}$C-NMR measurement (Varian Technologies Japan Ltd.: Varian-Unity 500). The results are shown below.

$[\alpha]^{26}{}_D$ +4.44° (c 0.495, MeOH)

FAB-MS: m/z 203 [M+H]$^-$ $^1$H NMR (500 MHz, CD$_3$OD): 1.30~1.55 (6H, m, H-5~H-8), 2.22 (2H, dq, J=1.6, 7.3 Hz, H-4), 3.41 (1H, dd, J=6.4, 11.0, H-10), 3.46 (1H, dd, J=4.6, 110, H-10), 3.56 (1H, m, H-9), 5.79 (1H, dt, J=15.6, 1.6 Hz, H-2), 6.95 (1H, dt, J=15.6, 7.1 Hz, H-3).

$^{13}$C-NMR (125 MHz, CD$_3$OD): 23.4, 29.2, 30.3, 33.0, 34.3 (C-4~C-8), 67.4 (C-10), 73.2 (C-9), 122.6 (C-2), 151.1 (C-3), 177.7 (C-1).

The result reveals that the compound contained in the D4-II-3E-4 fraction was identified as (2E)-9,10-dihydroxy-2-decenoic acid represented by the following formula. The (2E)-9,10-dihydroxy-2-decenoic acid is a component contained in an edible royal jelly. Thus, the component is considered safe, causing no side effects when orally ingested.

[Chem. 11]

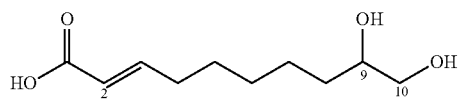

The obtained (2E)-9,10-dihydroxy-2-decenoic acid was methylated according to the method as shown in the following formula, and then treated with (S)-MTPACl to prepare (R)-MTPA ester. The $^1$H-NMR of the obtained (R)-MTPA ester was measured to calculate the surface ratio of the proton signal at the 10 position. As a result, it was found that the (2E)-9,10-dihydroxy-2-decenoic acid obtained as above was a racemic form, and the steric structures thereof were present in a ratio of R:S=3:1; considering calculation errors, the ratio fell within a range of at least R:S=2.8 to 3.8:1.

[Chem. 12]

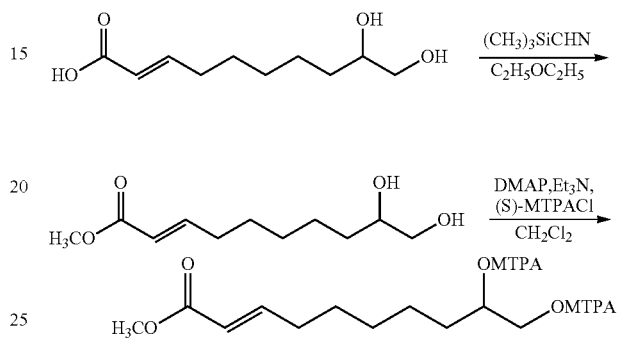

Preparation Example 2

See FIG. 7

Methanol (1,500 mL) was added to 200 g of a royal jelly dry powder (produced in Zhejiang province, Zhejiang, Pinghu), and the extraction was performed at room temperature with stirring for 12 hours. The eluent was filtrated under reduced pressure, and the solvent of the filtrate was distilled off under the reduced pressure. The resulting residue (108.9 g) was purified by ODS column chromatography (Column: Cosmosil 75C18-PREP; column size: ø80×205 mm; and eluent: 2,500 mL each of 10% and 50% methanol aqueous solutions (1,250 mL×2 fractions)), and divided into fraction 1 (the first half of the 10% methanol elution fraction); fraction 2 (the second half of the 10% methanol elution fraction); fraction 3 (the first half of the 50% methanol elution fraction); and fraction 4 (the second half of the 50% methanol elution fraction). The fraction 4 was purified by silica gel column chromatography (Column: Daiso gel IR-60; column size: ø26×150 mm; eluent: 500 ml of chloroform containing 5% methanol (50 mL×10 fractions)), and concentrated with the 7th to 10th eluted fractions. The obtained product was purified again by silica gel column chromatography (Column: Daiso gel IR-60; column size: ø26×150 mm; and eluent: 600 mL of chloroform containing 5% methanol (60 mL×10 fractions)). Then, the 5th eluted fraction was purified again by HPLC (Column: Cosmosil 5C18-AR column (Nacalai Tesque, 10×250 mm)); eluent: 0.1% TFA aqueous solution containing 13% acetonitrile; flow rate: 5.0 mL/min; and monitor: 220 nm) to obtain 13.3 mg of (2E)-9,10-dihydroxy-2-decenoic acid.

Preparation Example 3

Preparation of (2E,9S)-9-hydroxy-2-decenoic acid

Hereunder Also Referred to as "Compound DDA-14" for Convenience

[Chem. 13]

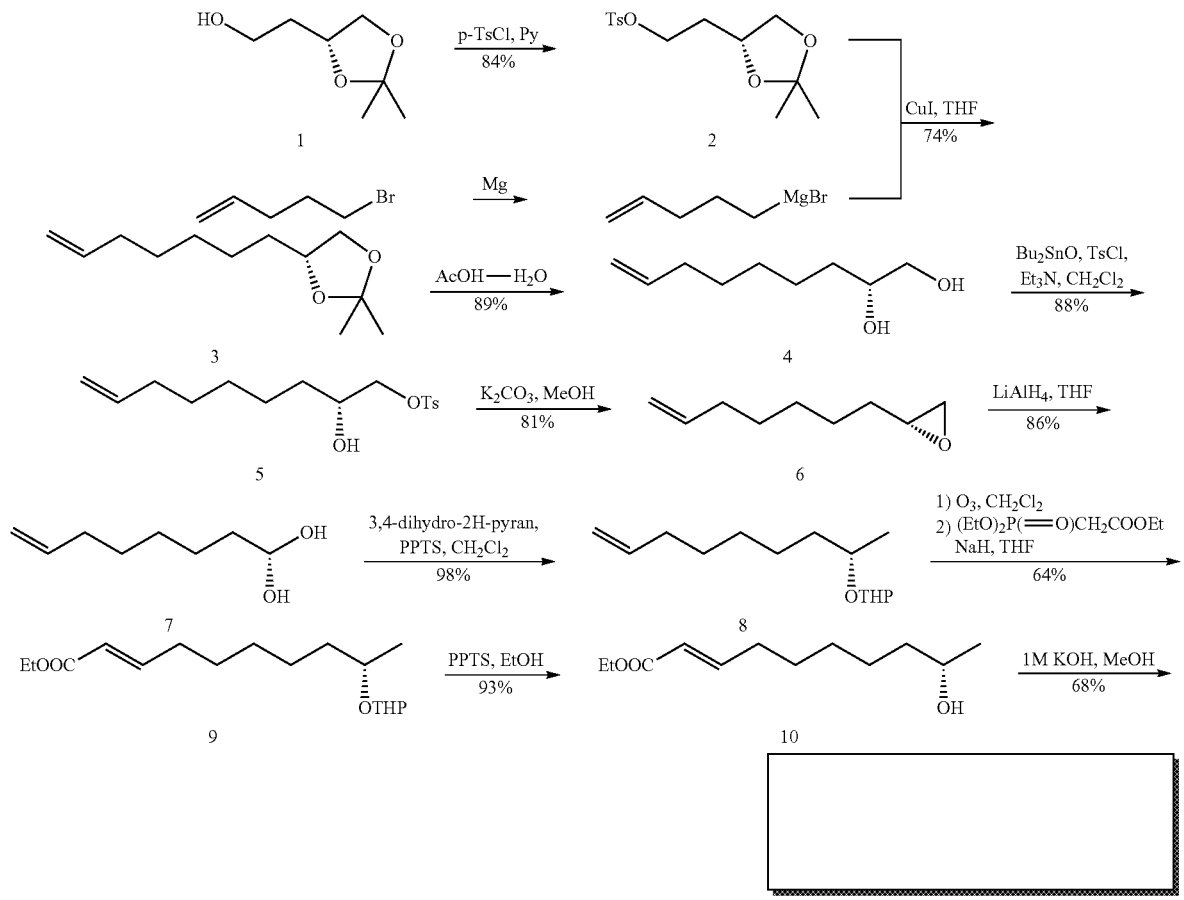

A commercially available (4R)-4-(2-hydroxyethyl)-2,2-dimethyl-1,3-dioxolane (1) was tosylated, and then subjected to a Grignard reaction with 5-bromo-1-pentene to prepare (R)-2,2-dimethyl-4-(oct-7-enyl)-1,3-dioxolane (3). Then, after the prepared product was treated with acetic acid and the acetonide was removed, the primary hydroxyl group was tosylated. Subsequently, ozonolysis followed by a Wittig reaction using trimethyl phosphonoacetate were performed, and the THP group was removed by acid hydrolysis with PPTS. Thereafter, alkali hydrolysis was performed using potassium hydroxide to synthesize the titled (2E,9S)-9-hydroxy-2-decenoic acid (11) (compound DDA-14).

The obtained compound DDA-14 was subjected to $^1$H-NMR measurement (JEOL Ltd.: Alpha-400). The results are shown below. $^1$H NMR (400 MHz, CD$_3$OD): 1.13 (d, J=6.0 Hz, 3H), 1.50-1.34 (m, 8H), 2.23-2.19 (m, 2H), 3.69 (m, 1H), 5.79 (dt, J=15.6, 1.4 Hz, 1H), 6.94 (dt, J=15.6, 6.8 Hz, 1H).

Preparation Example 4

Production of (2E,9R)-9-hydroxy-2-decenoic acid

Hereunder Also Referred to as "Compound DDA-15" for Convenience

[Chem. 14]

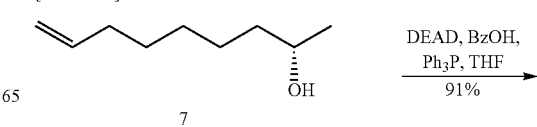

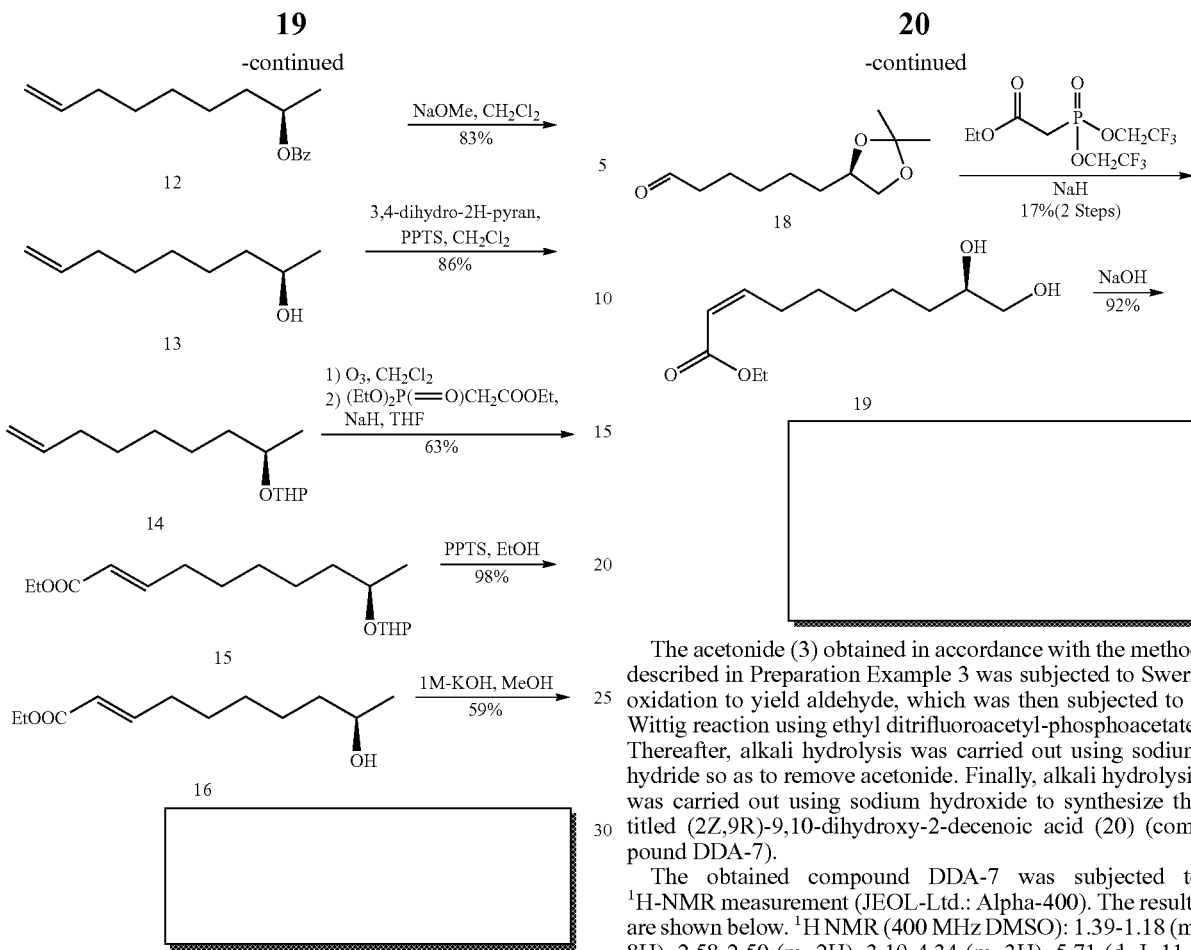

Alcohol (7) obtained in accordance with the method in Preparation Example 3 was subjected to a Mitsunobu reaction to invert the stereochemistry thereof to thereby obtain benzoate (12). Then, the titled (9R,2E)-9-hydroxy-2-decenoic acid (17) (compound DDA-15) was synthesized in the same method as in Preparation Example 3.

The obtained compound DDA-15 was subjected to $^1$H-NMR measurement (JEOL Ltd.: Alpha-400). The results are shown below. $^1$H NMR (400 MHz, CDCl$_3$): 1.03 (d, J=8.0 Hz, 3H), 1.44-1.20 (m, 8H), 2.17-2.11 (m, 2H), 3.62 (m, 1H), 5.71 (br.d, J=15.6 Hz, 1H), 6.86 (dt, J=15.6, 7.2 Hz, 1H).

Preparation Example 5

Preparation of (2Z,9R)-9,10-dihydroxy-2-decenoic acid

Hereunder Also Referred to as "Compound DDA-7" for Convenience

[Chem. 15]

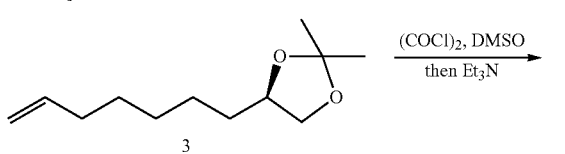

The acetonide (3) obtained in accordance with the method described in Preparation Example 3 was subjected to Swern oxidation to yield aldehyde, which was then subjected to a Wittig reaction using ethyl ditrifluoroacetyl-phosphoacetate. Thereafter, alkali hydrolysis was carried out using sodium hydride so as to remove acetonide. Finally, alkali hydrolysis was carried out using sodium hydroxide to synthesize the titled (2Z,9R)-9,10-dihydroxy-2-decenoic acid (20) (compound DDA-7).

The obtained compound DDA-7 was subjected to $^1$H-NMR measurement (JEOL-Ltd.: Alpha-400). The results are shown below. $^1$H NMR (400 MHz DMSO): 1.39-1.18 (m, 8H), 2.58-2.50 (m, 2H), 3.19-4.34 (m, 3H), 5.71 (d, J=11.6 Hz, 1H), 6.21 (dt, J=11.6, 7.6 Hz, 1H).

Preparation Example 6

Synthesis of (2E)-7-acetoxy-2-heptenoic acid

Hereunder Referred to as "Compound DDA-16" for Convenience

[Chem. 16]

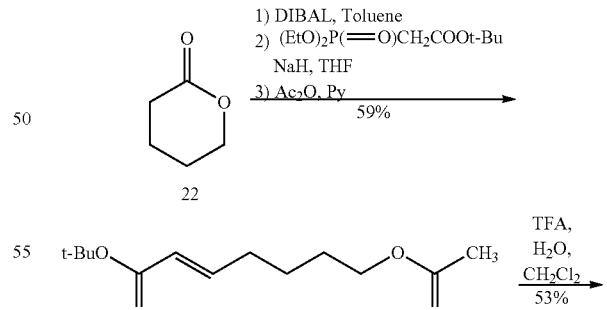

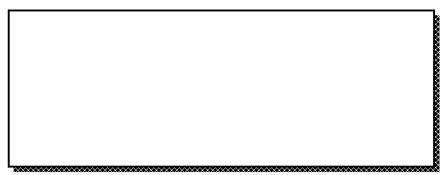

First, commercially available δ-valerolactone (22) was subjected to DIBAL reduction to yield aldehyde. Second, the Wittig reaction was performed using tert-butyl diethyl phosphonoacetate, and the obtained product was acetylated with acetic anhydride and pyridine. Finally, the t-BuO group was removed using trifluoroacetic acid to synthesize the titled (2E)-7-acetoxy-2-heptenoic acid (24) (DDA-16).

The obtained compound DDA-16 was subjected to $^1$H-NMR measurement (JEOL Ltd.: Alpha-400). The results are shown below. $^1$H NMR (400 MHz, $CDCl_3$): 1.71-1.52 (m, 4H), 2.05 (s, 3H), 2.30-2.21 (m, 2H), 4.07 (t, J=6.2 Hz, 2H), 5.85 (dt, 15.6, 1.6 Hz, 1H), 7.06 (dt, 15.6, 7.0 Hz, 1H).

Test Example 1

A forced swimming test has been widely used in the preclinical assessment of the antidepressant effect, and clinically effective antidepressants are known to shorten the immobility time (Porsort et al., Nature, 266, 730-732, 1977). Further, Okada et al. (Jpn. J. Pharmacology, 73: 93-96, 1997) and Yoshimura et al. (Brain Science 22: 49-54, 2000, Psychopharmacology 183: 300-307, 2005) have reported the following: when the ovaries are removed from a female animal to put the female animal in an artificial menopause state, the immobility time thereof is significantly increased; thus, the female animal that had been subjected to ovarian resection can be used as an animal model suffering from perimenopausal (menopausal) depressed mood or depressed state.

Therefore, the D4-II-3E-4 fraction ((2E)-9,10-dihydroxy-2-decenoic acid) prepared in Preparation Example 1 was administered to the animal model to undergo a forced swimming test (Nature, 266:730-732, 1977), and the antidepressant effect of the compound was evaluated.

(1) Preparation of Ovariectomy Animal Model

ICR female mice (9 weeks old; weight: 29 to 33 g) were used as experimental animals. All of the mice were group-housed (10 mice per cage), and the feed and white flake bedding were exchanged once per week. The surgery to remove the ovaries was performed according to the following method.

Ovarian Resection

Under pentobarbital anesthesia (65 mg/kg, i.p.), a 5 mm incision was made in the dorsal abdomen of a mouse, and the ovaries was temporarily exposed to the outside of the body. After ligation between the ovaries and uterus end (i.e. oviducts), the ovaries were dissected. Thereafter, the oviducts were promptly returned to the intraperitoneal cavity, and the abdominal wall and the skin were sutured.

(2) Administration of Test Substance

A 0.25 mg amount of the D4-II-3E-4 fraction (a freeze-dried product) prepared in Preparation Example 1 was dissolved in 50 ml of ion exchange water to prepare a suspension. The prepared suspension was orally administered using an oral sonde to each of the above-mentioned experimental animals (ovariectomy model mice) in an amount of 0.1 ml per 10 g of body weight once a day for 2 weeks from the day when the ovaries of each of the test animals were removed (test group). As a control experiment, distilled water for injection was orally administered in place of the D4-II-3E-4 fraction (a freeze-dried product) to each of the experimental animals (ovariectomy model mice) in an amount of 0.1 ml per 10 g of body weight (control group). Additionally, with respect to each of the mice with which a laparotomy had been performed similarly to the ovariectomy model mice mentioned above, but suture was carried out thereon without removing the ovaries, distilled water for injection was orally administered in an amount of 0.1 ml per 10 g of body weight to each of the mice (sham surgery group).

(3) Forced Swimming Test

Two weeks after the ovarian resection, the forced swimming test was carried out according to the method of Porsort et al. (Nature, 266: 730-732, 1977) with respect to each mouse of the test group, control group and sham surgery group in the following manner.

Water at a temperature of 25° C. was introduced into a clear measuring cylinder made of polycarbonate (inner diameter: 10 cm; height: 25 cm) so that the water surface level was adjusted to 10 cm from the bottom. Each mouse was forced to swim for 6 minutes while being recorded by a high-sensitivity video system. Thereafter, the recorded image was observed, and by means of an event recorder, the time (in seconds) during which the mouse was floating in an immobile state was measured (an analysis was made for the duration of the 4 minutes from the second minute onward).

(4) Experiment of Uterus Weight Measurement

After conducting the forced swimming test (after completing the observation of the immobility time), an overdose of pentobarbital (100 mg/kg or more) was administered to each of the mice to cause them to stop breathing, and the mice were sacrificed. Then, the uterus was collected from each of the mice through an incision in the abdomen. The collected uterus was spread onto a filter paper, and after the serosa and blood vessel adhering to the uterus were removed, the weight of the uterus was promptly measured on a wet basis with an analytical balance.

(5) Results

FIG. 8 shows the results. The results shows mean values with respect to 10 experimental animals each belonging to the test group (E-D4-II-3E-4 fraction), control group and sham surgery group. In the figure, the dashed line indicates a mean value with respect to the immobility time (in seconds) of the sham surgery group.

As shown in FIG. 8, the immobility time with respect to the experimental animals (ovariectomy model mouse) of the test group to which the D4-II-3E-4 fraction ((2E)-9,10-dihydroxy-2-decenoic acid) was administered was significantly shorter than that of the experimental animals of the control group to which the above-mentioned fraction was not administered. This reveals that (2E)-9,10-dihydroxy-2-decenoic acid exhibits an antidepressant effect, in particular an antidepressant effect effective for improving depressed mood and depressed state in menopausal women.

Further, as shown in FIG. 9, a difference in the uterus weights was not recognized between the experimental animals (ovariectomy model mice) of the test group to which the D4-II-3E-4 fraction ((2E)-9,10-dihydroxy-2-decenoic acid) was administered at a dose that would shorten the immobility time, and the experimental animals of the control group.

It has been reported that when an estrogen, a female sex hormone, is administered to a female animal whose ovaries have been removed, the immobility time will be shortened, and will return to the normal value (Bekku, Yoshimura et al., Japanese Journal of Psychopharmacology, 22: 298, 2002; and Psychopharmacology 183: 300-307, 2005). This indicates that an estrogen improves a perimenopausal "depressed state". However, it is also known that an estrogen administration results in a significant increase in the uterus weight of a female animal whose ovaries have been removed, compared to that of a female animal whose ovaries have not been removed. This means that an estrogen administered in an amount that can improve a "depressed state" will exert an adverse effect of abnormally increasing the uterus weight.

The abnormal increase in the uterus weight attributable to an estrogen is considered equivalent to the symptoms of adverse effects described in human hormone replacement therapy.

With reference to the results shown in FIGS. 8 and 9, the D4-II-3E-4 fraction ((2E)-9,10-dihydroxy-2-decenoic acid) obtained above effectively improves immobility time with a greatly minimized risk of adverse effects of, for example, increasing uterus weight. Accordingly, it was clarified that the D4-II-3E-4 fraction exhibits an antidepressant effect effective for improving menopausal depressed mood or depressed state in women.

FIG. 10 shows the results of a forced swimming test carried out in the same manner as above using 10-hydroxydecenoic acid (10-HDA, comparative compound) as a test substance. The results clarify that 10-hydroxydecenoic acid does not exhibit an antidepressant effect and that therefore, an antidepressant effect is an effect specific to (2E)-9,10-dihydroxy-2-decenoic acid.

Test Example 2

Test Example 1 was partly modified as below, and a forced swimming test was performed to evaluate an antidepressant effect using the compounds (DDA-7 and DDA-14 to DDA-16) prepared in Preparation Examples 3 to 6 as test compounds. Regarding DDA-14 and DDA-15, a naturally occurring racemic form thereof has been reported, and thus, similarly to the mixture ratio by weight thereof, DDA-14 and DDA-15 were mixed at the ratio of 3:1 and prepared (2E,9S+9R)-9-hydroxy-2-decenoic acid (racemic form).

(1) Forced Swimming Test

The experimental animals (ovariectomy model mice), to which each test compound was administered for 14 days (the first day of the administration was the following day after the day the ovaries were removed), were forced to swim. A 0.32 mg amount of compound DDA-7, 0.29 mg and 0.088 mg of DDA-14 and DDA-15, respectively, and 0.29 mg of DDA-16 were each individually dissolved in 80 ml of ion exchange water for administration. On the 14th day from the day each test compound administration was commenced, and 2 hours after the test compound was orally administered, each of the experimental animals was placed into a water tank, and the swimming time was measured for 10 minutes (test group). As a control experiment, the same procedure was performed as above, except that distilled water for injection was orally administered in place of the test compounds to each of the experimental animals (ovariectomy model mouse) in an amount of 0.1 ml per 10 g of body weight (control group).

The swimming time was measured in the following manner: a mouse on which magnets were attached to both of the hind legs was placed into a water tank (diameter: 145 mm; height: 190 mm; water depth: 100 mm; water temperature: about 24±2° C.), and the movement of the hind legs was observed for 10 minutes using an itch-measuring system (Neuroscience Co., Ltd.). The ten-minute swimming time was divided into one-minute periods to conduct analysis.

(2) Results

The following table and FIG. 11 show the immobility time measured during the period from the 2nd minute to the 4th minute. The results represent mean values of 6 experimental animals each belonging to the test group and control group.

TABLE 1

| Immobility Time | Control | Test Group | | |
| --- | --- | --- | --- | --- |
| (second) | Group | DDA-7 | DDA14 + DDA15 | DDA-16 |
| Mean | 109.06 | 80.14 | 98.82 | 87.14 |
| SD | 3.77 | 10.4 | 4.93 | 4.34 |

As the results show, the immobility time of the experimental animals (ovariectomy model mice) of the test group to which each of the above-mentioned test compounds was administered was significantly shorter than that of the experimental animals of the control group to which the test compound was not administered. In view of this, it is clear that compounds DDA-7 and DDA-16, which were prepared in Preparation Examples 3 and 6, and a racemic mixture of compounds DDA-14 and DDA-15 exhibit an antidepressant effect, in particular an antidepressant effect effective for improving menopausal depressed mood or depressed state in women.

Example 1 to 4

Capsule

| | |
| --- | --- |
| (2E)-9,10-dihydroxy-2-decenoic acid (Preparation Example 1) | 5 mg |
| Purified dry yeast (Asahi Beer Chemical Kabushiki Kaisha) | 344 mg |
| Sucrose fatty acid ester (Taiyo Kagaku Co., Ltd.) | 1 mg |

The above components (powder) were homogeneously mixed, and 350 mg of the obtained powder was filled in a hard capsule No. 1 to thereby prepare a capsule (Example 1).

Capsules were prepared in the same manner as above, except that, in place of (2E)-9,10-dihydroxy-2-decenoic acid (Preparation Example 1), the mixture of DDA-14 and DDA-15 (natural racemic mixture) ((2E,9S+9R)-9-hydroxy-2-decenoic acid) synthesized in Preparation Examples 3 and 4, DDA-7 ((2Z,9R)-9,10-dihydroxy-2-decenoic acid) synthesized in Preparation Example 5, and DDA-16 ((2E)-7-acetoxy 2-heptenoic acid) synthesized in Preparation Example 6 were used.

Examples 5 to 8

Drink

| | |
| --- | --- |
| (2E)-9,10-dihydroxy-2-decenoic acid (Preparation Example 1) | 5 mg |
| Lemon juice (Pokka Corporation) | 20 ml |
| Propolis (API Co., Ltd.) | 0.2 g |
| Vitamin C (Takeda Pharmaceutical Company Limited) | 0.2 g |
| Honey (API Co., Ltd.) | 13 g |

The above-mentioned five components were dissolved in water, and then poured into a brown bottle to thereby prepare a drink (100 ml per bottle).

Drinks were prepared in the same manner as above, except that, in place of (2E)-9,10-dihydroxy-2-decenoic acid (Preparation Example 1), the mixture of DDA-14 and DDA-15 (a natural racemic mixture) ((2E,9S+9R)-9-hydroxy-2-decenoic acid) synthesized in Preparation Examples 3 and 4, DDA-7 ((2Z,9R)-9,10-dihydroxy-2-decenoic acid) synthesized in Preparation Example 5, and DDA-16 ((2E)-7-acetoxy 2-heptenoic acid) synthesized in Preparation Example 6 were used (Examples 6 to 8).

Examples 9 to 12

Hard Capsule

| | |
|---|---:|
| (2E)-9,10-dihydroxy-2-decenoic acid (Preparation Example 1) | 5 mg |
| Lactose (API Co., Ltd.) | 150 mg |
| Theanine (TAIYO KAGAKU CO., LTD.) | 50 mg |

The above components (powder) were homogeneously mixed, and 350 mg of the obtained powder was filled in a hard gelatin capsule No. 1 to prepare a capsule.

Capsules were prepared in the same manner as above, except that, in place of (2E)-9,10-dihydroxy-2-decenoic acid (Preparation Example 1), the mixture of DDA-14 and DDA-15 (a natural racemic mixture) ((2E,9S+9R)-9-hydroxy-2-decenoic acid) synthesized in Preparation Examples 3 and 4, DDA-7 ((2Z,9R)-9,10-dihydroxy-2-decenoic acid) synthesized in Preparation Example 5, and DDA-16 ((2E)-7-acetoxy 2-heptenoic acid) synthesized in Preparation Example 6 were individually used (Examples 10 to 12).

Examples 13 to 16

Drink

| | |
|---|---:|
| (2E)-9,10-dihydroxy-2-decenoic acid (Preparation Example 1) | 5 mg |
| Honey (API Co., Ltd.) | 7,500 mg |
| Siberian ginseng extract (Yakuhan Pharmaceutical Co., Ltd.) | 2,500 mg |
| Propolis extract (API Co., Ltd.) | 1,000 mg |
| Vitamin C (Takeda Chemical, Ltd.) | 300 mg |
| Citric acid (API Co., Ltd.) | 100 mg |

The above-mentioned six components were dissolved in water, and then poured into a brown bottle to prepare a drink (30 ml per bottle).

Drinks were prepared in the same manner as above, except that, in place of (2E)-9,10-dihydroxy-2-decenoic acid (Preparation Example 1), the mixture of DDA-14 and DDA-15 (a natural racemic mixture) ((2E,9S+9R)-9-hydroxy-2-decenoic acid) synthesized in Preparation Examples 3 and 4, DDA-7 ((2Z,9R)-9,10-dihydroxy-2-decenoic acid) synthesized in Preparation Example 5, and DDA-16 ((2E)-7-acetoxy 2-heptenoic acid) synthesized in Preparation Example 6 (Examples 2 to 4) were individually used (Examples 14 to 16).

INDUSTRIAL APPLICABILITY

The present invention provides a novel compound that has an antidepressant effect, and that is effective as an active ingredient in a pharmaceutical composition, particularly in an antidepressant. The present invention further provides an antidepressant composition comprising the above compound as an active ingredient. In particular, the antidepressant composition can be effectively used for improving menopausal depressed mood and depressed state in women.

BRIEF DESCRIPTION OF THE DRAWINGS

FIG. 7 is a flow chart showing a method employed in Preparation Example 2 for isolating and purifying (2E)-9,10-dihydroxy-2-decenoic acid from dried royal jelly powder.

FIG. 8 is a graph showing the result of the immobility time (in seconds) measured during a forced swimming test performed with respect to the ovariectomy model mice to which D4-II-3E-4 fraction (a freeze-dried product) prepared in Preparation Example 1 was orally administered (test group) (black bar), and the ovariectomy model mice to which distilled water was orally administered (control group) (white bar). The dashed line indicates a mean value of the immobility time (in seconds) with respect to the sham surgery group.

Figure 1:
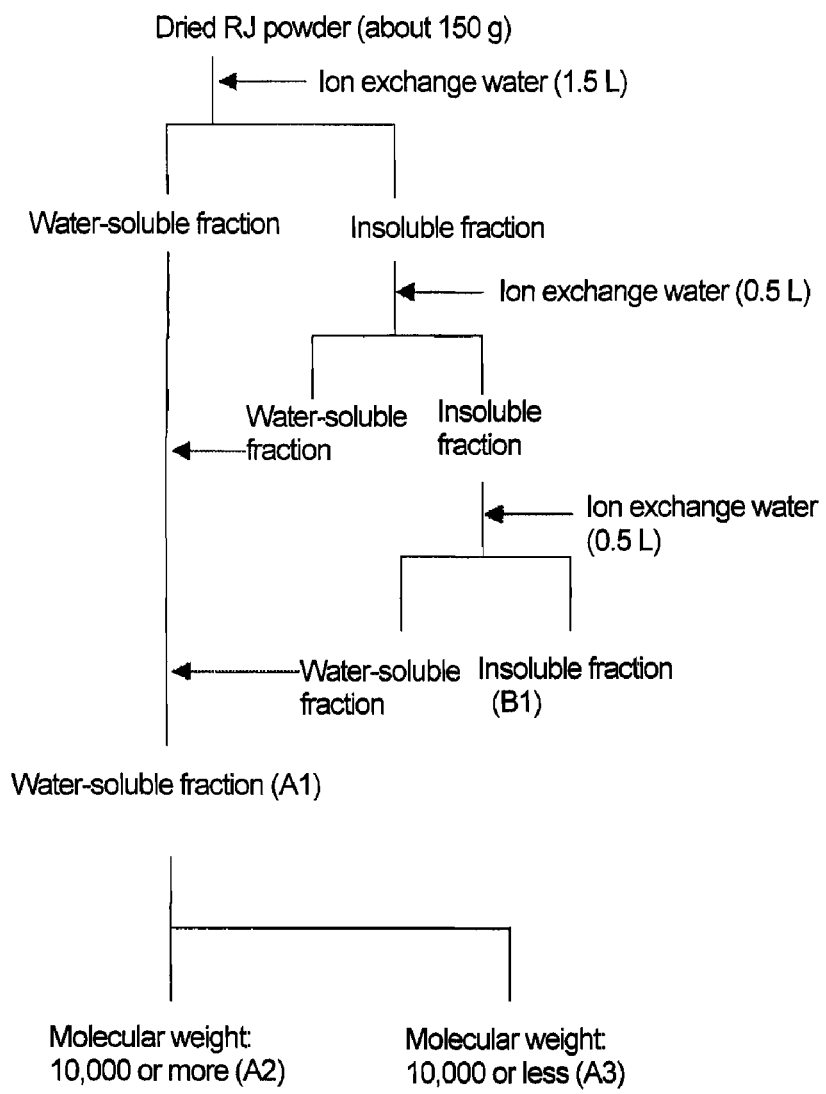
FIG. 1 illustrates a process of "preparing A3 fraction using an ultrafiltration membrane" in the process of isolating and purifying (2E)-9,10-dihydroxy-2-decenoic acid from dried royal jelly powder.
Figure 2:
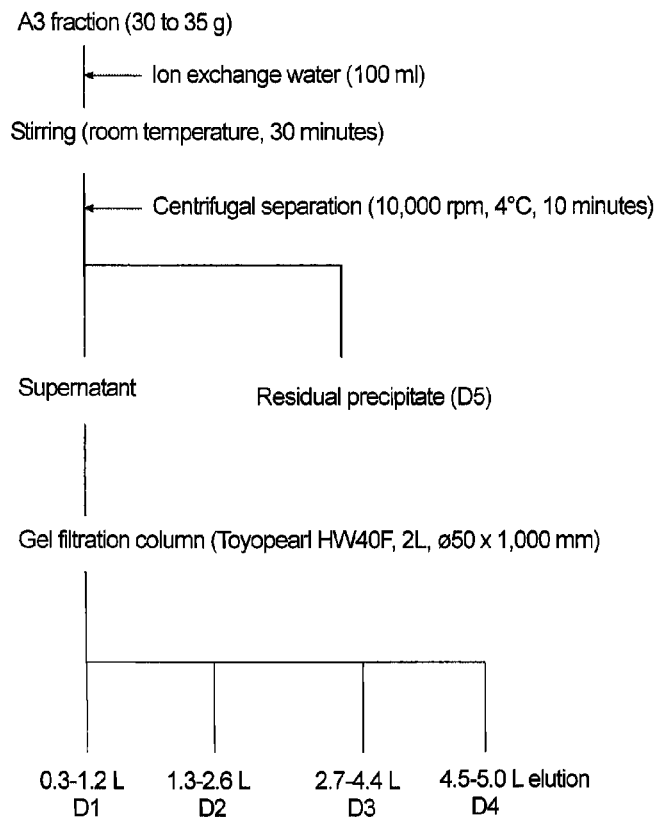
FIG. 2 illustrates a process of "fractionation from A3 fraction by gel filtration" in the process of isolating and purifying (2E)-9,10-dihydroxy-2-decenoic acid from dried royal jelly powder.
Figure 3:
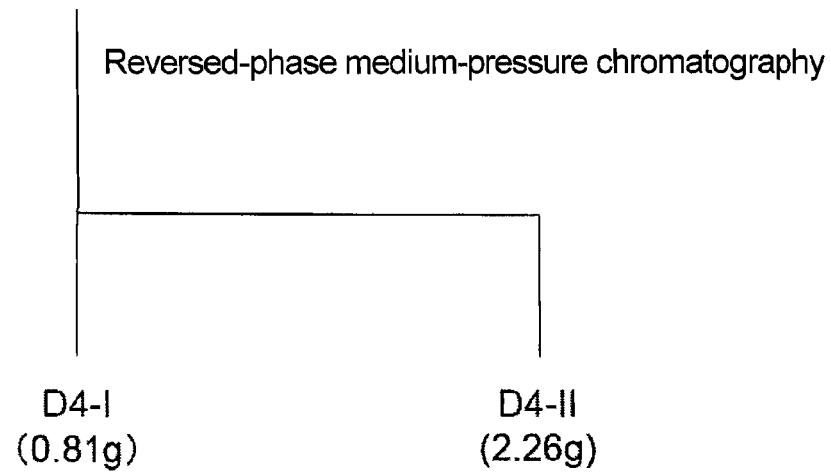
FIG. 3 illustrates a process of "fractionation from D4 fraction by reversed-phase (ODS) medium-pressure chromatography" in the process of isolating and purifying (2E)-9,10-dihydroxy-2-decenoic acid from dried royal jelly powder.
Figure 4:
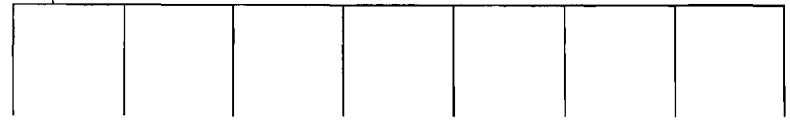
FIG. 4 illustrates a process of "fractionation from D4-II fraction by reversed-phase (ODS) high-performance liquid chromatography" in the process of isolating and purifying (2E)-9,10-dihydroxy-2-decenoic acid from dried royal jelly powder.
Figure 5:
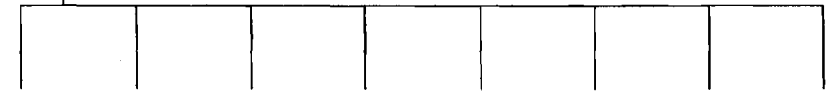
FIG. 5 illustrates a process of "fractionation from D4-II-3 fraction by reversed-phase (ODS) high-performance liquid chromatography" in the process of isolating and purifying (2E)-9,10-dihydroxy-2-decenoic acid from dried royal jelly powder.
Figure 6:
FIG. 6 illustrates a process of "separation from D4-II-3E fraction by the normal phase chromatography" in the process of isolating and purifying (2E)-9,10-dihydroxy-2-decenoic acid from dried royal jelly powder.
Figure 9:
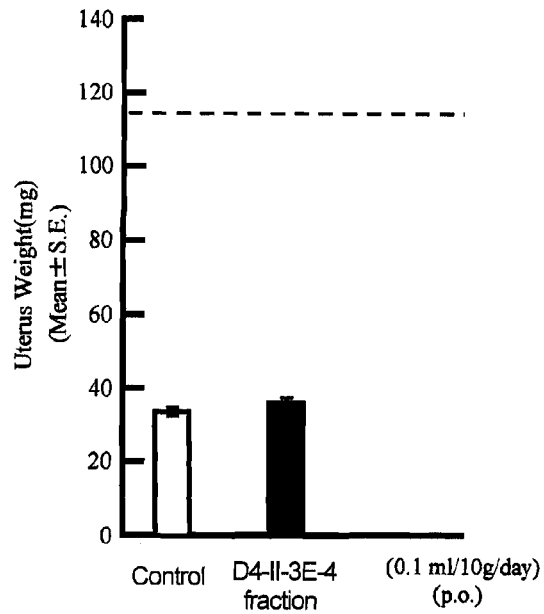
FIG. 9 is a graph showing the measurement result of uterus weights on which D4-II-3E-4 fraction ((2E)-9,10-dihydroxy-2-decenoic acid) in an amount that shortens the immobility time was acted. A vertical axis represents the uterus weight (mg). A dashed line indicates a uterus weight (normal value) of the sham surgery group in which the ovaries were not removed.
Figure 10:
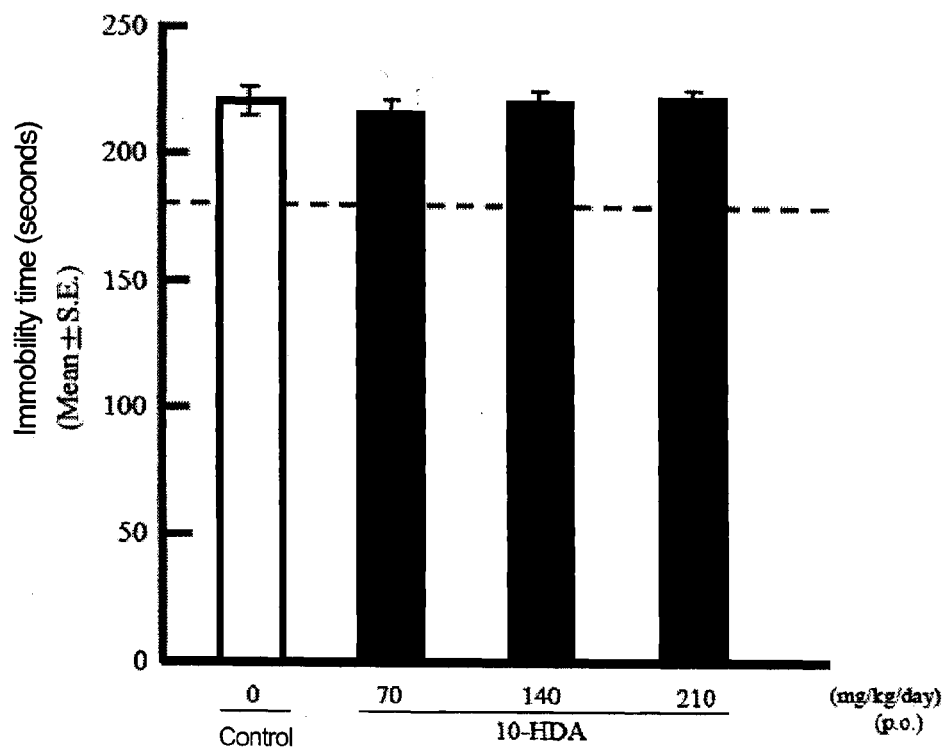
FIG. 10 is a graph showing the result of the immobility time (in seconds) measured during a forced swimming test performed with respect to the ovariectomy model mice to which 10-hydroxydecenoic acid (10-HDA) was orally administered (70, 140, 210 mg/kg/day) (test group) (black bar), and the ovariectomy model mice to which distilled water was orally administered (control group) (white bar). The dashed line indicates a mean value of the immobility time (in seconds) with respect to the sham surgery group.
Figure 11:
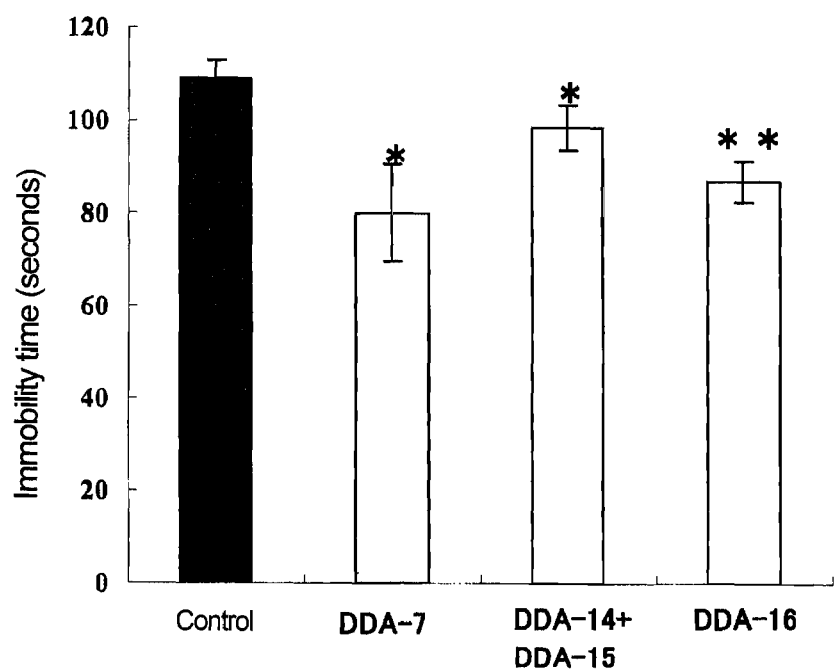
FIG. 11 is a graph showing the result of the immobility time (in seconds) measured during a forced swimming test performed with respect to the ovariectomy model mice to which a mixture of DDA-14 and DDA-15 (a natural racemic mixture) ((2E,9S+9R)-9-hydroxy-2-decenoic acid) synthesized in Preparation Examples 3 and 4, DDA-7 ((2Z,9R)-9,10-dihydroxy-2-decenoic acid) synthesized in Preparation Example 5, and DDA-16 ((2E)-7-acetoxy 2-heptenoic acid) synthesized in Preparation Example 6 were orally adminis-

The invention claimed is:

1. A carboxylic acid represented by the following formula (1):

[Chem. 1]

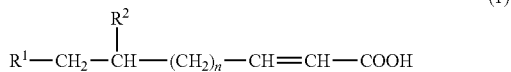
(1)

wherein $R^1$ represents a hydroxyl group, $R^2$ represents a hydroxyl group or an acetyloxy group, wherein $R^1$ and $R^2$ may be the same or different, and n is an integer of 2 to 7, or a pharmaceutically acceptable salt, $C_1$ to $C_6$ lower alkyl ester or $C_1$ to $C_6$ lower alkyl thioester thereof.

2. The carboxylic acid, or the pharmaceutically acceptable salt, $C_1$ to $C_6$ lower alkyl ester or $C_1$ to $C_6$ lower alkyl thioester thereof according to claim 1, wherein the carboxylic acid is a compound selected from the group consisting of (2E)-9,10-dihydroxy-2-decenoic acid and (2Z)-9,10-dihydroxy-2-decenoic acid.

3. The carboxylic acid, or the pharmaceutically acceptable salt, $C_1$ to $C_6$ lower alkyl ester or $C_1$ to $C_6$ lower alkyl thioester thereof according to claim 2, wherein the (2E)-9,10-dihydroxy-2-decenoic acid is (2E,9R)-9,10-dihydroxy-2-decenoic acid or (2E,9S)-9,10-dihydroxy-2-decenoic acid.

4. The carboxylic acid, or the pharmaceutically acceptable salt, $C_1$ to $C_6$ lower alkyl ester or $C_1$ to $C_6$ lower alkyl thioester thereof according to claim 2, wherein the (2Z)-9,10-dihydroxy-2-decenoic acid is (2Z,9R)-9,10-dihydroxy-2-decenoic acid or (2Z,9S)-9,10-dihydroxy-2-decenoic acid.

5. A pharmaceutical composition comprising, as an active ingredient, the carboxylic acid, or the pharmaceutically acceptable salt, $C_1$ to $C_6$ lower alkyl ester or $C_1$ to $C_6$ lower alkyl thioester thereof in accordance with any of claims 1 to 4.

6. A method for improving depressed mood or depressed state, comprising administering a carboxylic acid of any one of claims 1 to 4 or a pharmaceutically acceptable salt, $C_1$ to $C_6$ lower alkyl ester or $C_1$ to $C_6$ lower alkyl thioester thereof, to a person in a depressed mood or depressed state.

7. A mixture of carboxylic acids comprising (2E,9R)-9,10-dihydroxy-2-decenoic acid and (2E,9S)-9,10-dihydroxy-2-decenoic acid.

8. A mixture of carboxylic acids comprising (2Z,9R)-9,10-dihydroxy-2-decenoic acid and (2Z,9S)-9,10-dihydroxy-2-decenoic acid.

* * * * *